(12) United States Patent  (10) Patent No.: US 6,692,124 B2
Katz et al.  (45) Date of Patent: Feb. 17, 2004

(54) EYEWEAR WITH VENTILATION

(76) Inventors: Robert Katz, 1648 C Sherbrooke Street West, Montreal, Quebec (CA), H3H 1C9; Brent Sheldon, 315 Putney, St. Lambert, Quebec (CA), J4P 2B5

( * ) Notice: Subject to any disclaimer, the term of this patent is extended or adjusted under 35 U.S.C. 154(b) by 0 days.

(21) Appl. No.: 10/147,962

(22) Filed: May 20, 2002

(65) Prior Publication Data

US 2003/0214626 A1 Nov. 20, 2003

(51) Int. Cl.7 .............................................. G02C 11/08
(52) U.S. Cl. ................. 351/62; 2/435; 2/436
(58) Field of Search ................. 351/41, 62; 2/435, 2/436, 437

(56) References Cited

U.S. PATENT DOCUMENTS

| 2,027,037 A | | 1/1936 | Gottlieb | |
|---|---|---|---|---|
| 3,708,224 A | | 1/1973 | Lindblom | |
| 4,405,212 A | * | 9/1983 | Cooper | 351/43 |
| 4,707,863 A | | 11/1987 | McNeal | |
| 5,245,709 A | | 9/1993 | Shipcott | |
| 6,149,268 A | | 11/2000 | Hall et al. | |
| 6,257,719 B1 | | 7/2001 | Pavlak | |
| 6,276,795 B1 | | 8/2001 | Hall et al. | |
| 6,450,639 B1 | * | 9/2002 | Abraham | 351/62 |

FOREIGN PATENT DOCUMENTS

JP  4-75019  * 3/1992  ................ 351/62

* cited by examiner

Primary Examiner—Huy Mai
(74) Attorney, Agent, or Firm—Ogilvy Renault

(57) ABSTRACT

Protective eyewear of the invention includes at least one lens and a frame securing the lens. Temples or a retention strap are provided for attaching the protective eyewear to the head of a user. The frame includes a seal member around the lens with ventilation channels formed in the seal member on its surface for contacting the face of the user. Thus, the seal member forms a substantial enclosure between the lens and the face of the user when the eyewear is worn. The ventilation channels extend into the seal member towards the lens to a depth not reaching the lens and ensure free passage of air from the enclosure to the atmosphere so that moisture condensation on the lens is reduced or eliminated.

17 Claims, 2 Drawing Sheets

EYEWEAR WITH VENTILATION

FIELD OF THE INVENTION

The present invention relates generally to eyewear, and more particularly relates to eyewear with ventilation.

BACKGROUND OF THE INVENTION

Protective eyewear is available in the market place for both safety and recreational applications. The lenses of eyewear are often in direct contact with or are disposed in closely spaced relationship to certain areas of the face of the user, such as the cheeks and the super-orbital arches. In such cases when the face perspires and the lenses are relatively cool, or when the lenses are worn from a cold atmosphere into a warm moist atmosphere, moisture condenses on the surfaces of the lenses next to the face, and especially on areas thereof at or adjacent to the point of contact between the lenses and the face. Thus, the lenses of the eyewear become clouded with condensation so as to seriously interfere with vision therethrough.

It is well know that providing a free circulation of air over the surface of the lens between the lens and the face of the user can substantially reduce or inhibit such condensation of moisture.

U.S. Pat. No. 2,027,037, issued to Gottlieb on Jan. 7, 1936 describes VENTILATED SPECTACLES OR EYEGLASSES which have ventilation slots disposed between the outer peripheries of the lenses and the outer peripheries of the lens-receiving rims, or which have an air passage formed by the spaces between the lens-receiving rims and the guides that partially surround the lenses and are disposed at the sides of the rims next to the face of the user while the spectacles are worn. However, Gottlieb's ventilated spectacles or eyeglasses are generally not proper for use as protective eyewear, and do not provide seals between the lenses and the face of the user while Gottlieb's spectacles or eyeglasses are worn.

U.S. Pat. No. 6,149,268, issued to Hall et al. on Nov. 21, 2000 describes PROTECTIVE EYEWEAR WITH AT LEAST ONE VENTILATION CHANNEL which is provided with particulate sealing around a frame containing a lens and having temples. A plurality of ventilation channels are disposed on the frame to provide indirect ventilation. The ventilation channels are formed in the frame on the side thereof contacting the lens.

U.S. Pat. No. 4,707,863, issued to McNeal on Nov. 24, 1987 describes ANTI-FOG GOGGLE WITH FOAM FRAME which also includes slotted rims on the goggle for providing ventilation channels. McNeal's slots are disposed on the outside of the cushion rim, adjacent to the plastic shield of the goggle.

In order to prevent sweat drippings from entering the top ventilation slots or channels and flowing down along the interior surface of the lens or shield of Hall et al's protective eyewear or McNeal's anti-fog goggle, an elongate lip, as described by Hall et al., or an upper bead as described by McNeal, must be provided along portions of the frame above the top ventilation slots or channels, which makes the entire structure of the Hall et al's eyewear and McNeal's goggle relatively complicated. Therefore, a simpler configuration for eyewear with ventilation is desirable

SUMMARY OF THE INVENTION

It is one object of the present invention to provide eyewear with ventilation.

It is another object of the present invention to provide a simple configuration for protective eyewear with ventilation.

In accordance with one aspect of the present invention, eyewear comprises at least one lens, a frame securing the at least one lens and means for attaching the eyewear to the head of a user. The frame includes a seal member having a surface for contacting the face of the user. The seal member forms a substantial enclosure between the at least one lens and the face of the user when the surface of the seal member contacts the face of the user. At least one ventilation channel is formed in the seal member on the surface for contacting the face of the user. The ventilation channel extends into the seal member towards the lens to a depth not reaching the lens and ensuring free passage of air from the enclosure to the atmosphere when the user wears the eyewear.

The ventilation channel is preferably one of a plurality of ventilation channels in the seal member. At least one of the ventilation channels is preferably located in a bottom section of the seal member. It is also preferable that at least one of the ventilation channels is located in a top section of the seal member. The means for attaching the eyewear to the head of the user in accordance with one embodiment comprise a pair of temples pivotally attached to opposite sides of the frame, and in accordance with another embodiment of the present invention comprise a retention strap attached to opposite sides of the frame.

The present invention provides a simple configuration for eyewear with ventilation. The seal member with ventilation channels provides means for regulating air flow around the user's eyes in order to reduce moisture condensation on the lenses of eyewear and provides protection of eyes from relatively large particles. The seal member further provides a cushion for the user of the eyewear against impact which may occur to the eyewear.

Other features and advantages can be better understood with reference to preferred embodiments described hereinafter.

BRIEF DESCRIPTION OF THE DRAWINGS

Having thus generally described the nature of the present invention, reference will now be made to the accompanying drawings, showing by way of illustration the preferred embodiments thereof, in which.

DETAILED DESCRIPTION OF THE PREFERRED EMBODIMENTS

Figure 1:
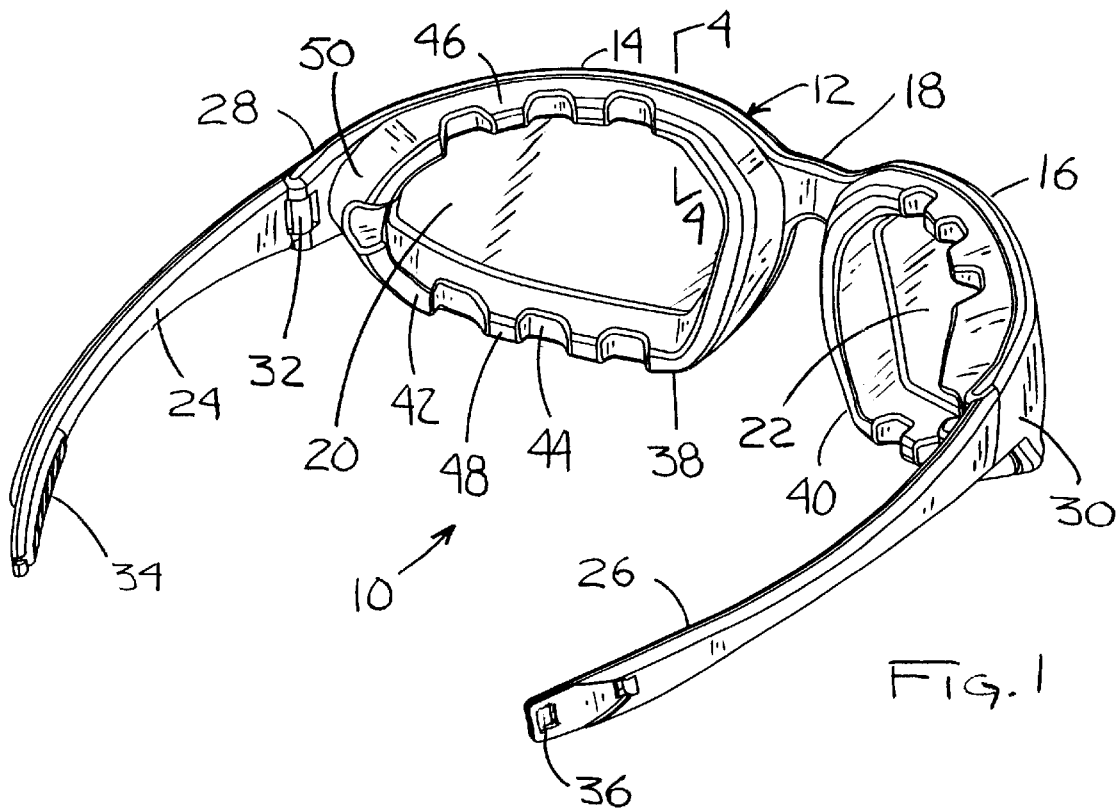
FIG. 1 is a perspective view of protective eyewear according to a first embodiment of the present invention, showing ventilation channels formed on the contacting surface of the seal member, and positioned in both top and bottom sections thereof.

With reference to the drawings and in particular to FIG. 1, a eyewear structure in accordance with a first embodiment of the present invention, generally designated by reference numeral 10, includes a frame structure 12 having two frame sections 14, 16 with a bridge 18 connected between an inner side of the frame sections 14, 16. Each of the frame sections 14, 16 has a lens 20 or 22 fixed therein. The frame sections 14, 16 have inner grooves 21, as shown in FIGS. 4A–4D, for holding the lenses 20 and 22, in respective frame sections 14, 16, which is well known in the art and will not be further described. A pair of temples 24, 26 are pivotally mounted to opposite sides 28, 30 of the frame 12 by means of a hinge assembly 32 (only one shown). A plurality of contacting ribs 34 are provided on the inner side at the free end of the temples 24, 26 for comfortably holding the eyewear structure 10 on the user's head when the eyewear are worn. An aperture 36 is also provided through each of the temples 24, 26 at its free end for optionally attaching an elastic strap (not shown) for further securing the eyewear structure 10 on the user's head when the eyewear are worn.

Seal members 38, 40 are attached to the respective frame sections 14, 16 on their inner side. The seal members 38, 40 are identical and the description will be made with reference only to seal member 38 for precision and convenience of description.

The seal member 38 protrudes from the inner side of the frame section 14 and extends around the lens 20. The seal member 38 has a contacting surface 42 which is contoured for comfortably contacting a portion of the face around the eye of the user when the eyewear structure 10 is worn. Thus, the seal member 38 forms a substantial enclosure between the lens 20 and the face of the user when the contacting surface 42 of the seal member 38 contacts the face of the user. It should be noted that a proper seal between the seal member 38 and the face of the user is achieved by the secure attachment of the eyewear, which can be assured by the optional elastic strap attached to the aperture 36 of the temples 24, 26, particularly when the temples 24, 26 have a relatively short length.

Ventilation channels 44 are formed on the contacting surface 42 of the seal member 38, and are positioned in both top section 46 and bottom section 48 as well as in the outer side section 50 of the seal member 38, in order to ensure free passage of air from the enclosure to the atmosphere when the user wears the eyewear structure 10, so that air flow around the eyes of the user eliminates or reduces moisture condensation on the lens 20. Each of the ventilation channels 44 extends into the seal member towards the lens 20 to a depth which is determined according to the depth of the seal member that is the distance between the contacting surface 42 and the inner side of the frame section 14, and is also determined by the softness of the seal member 38.

The seal member 38 can be made of various materials. For example, the seal member 38 can be made of semi-solid plastic in a hollow configuration as indicated by numeral 38A in FIG. 4A. The hollow seal member 38A with channels 44 thereon is molded in one process so that the hollow configuration of the seal member 38A forms a closed chamber 52 therein and the channels 44 do not provide openings of the closed chambers 52. The resilient property of the semi-rigid plastic and the air trapped in the closed chamber 52 provides a resilient deformation of the hollow seal member 38A when the eyewear structure 10 is worn and the seal member 38A is compressed.

Figure 4A:
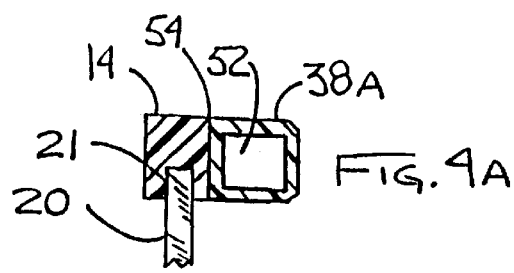
FIGS. 4A–4D are cross-sectional views taken along line 4—4 in FIG. 1, showing the cross-section of the frame and the seal member.
Figure 4C:
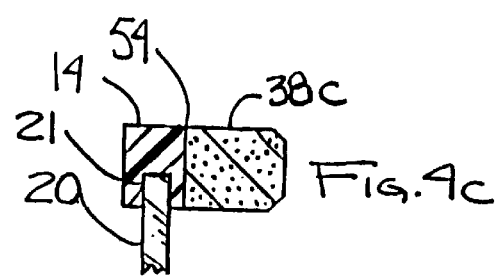
Figure 4B:
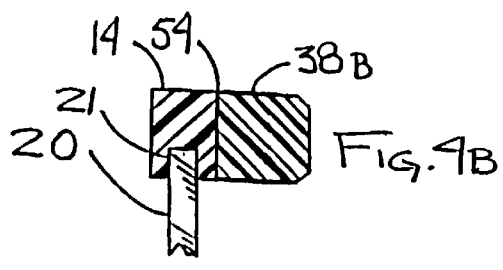

The seal member in another example can be made of elastomeric rubber as indicated by numeral reference 38B in FIG. 4B.

In a further example as illustrated in FIG. 4C, the seal member indicated by numeral reference 38C can be made of a plastic foam, such as sponge.

The seal member of the present invention when formed from different materials has different elastic properties and different softness, which provides options for designing the eyewear structure 10 to meet various requirements of different applications.

The ventilation channels 44 must have a sufficient depth to ensure the free passage of air therethrough while the eyewear structure 10 is being worn and the seal member 38 is being deformed by the compression of the seal member 38 caused by a holding force, for example, of an elastic strap. Generally, the ventilation channels 44 should be deeper when the seal member 38 is softer. Nevertheless, the ventilation channels 44 should not extend the entire depth of the seal members 38 to reach the inner side of the frame section 14. Ventilation channels 44 extending through the entire depth of the seal member 38 would divide a single seal member 38 into several sections, which would increase the difficulty of manufacturing the eyewear structure 10 compared to a single piece seal member 38 attached to the frame section 14. Furthermore, sweat drippings entering the ventilation channels 44 in the top section 46 of the seal member 38 might flow along the interior surface of the lens 20 which is not desirable.

Figure 4D:
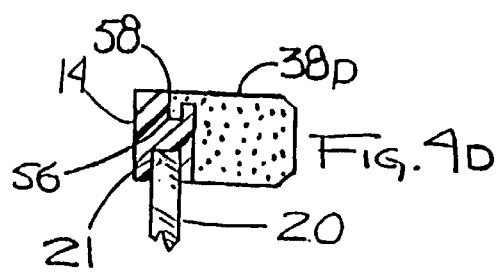

There are numerous ways of attaching the seal member 38 to the frame section 14. A simple and general approach is illustrated in FIGS. 4A–4C, in which the respective seal members 38A, 38B and 38C are secured to the inner side of the frame section 14 by means of adhesives 54 applied to the interfaces of the frame section 14 and the seal member 38A, 38B or 38C. Optionally, as illustrated in FIG. 4D, the frame section 14 further includes an annular groove 56 around its outer periphery and the seal member 38D includes a flange 58 having an L-shaped cross-section extending along the outer peripheral edge thereof. Thus, the seal member 38D is secured to the frame section 14 when the L-shaped flange 58 engages in the annular groove 56 of the frame section 14. Adhesives (not shown) can be optionally applied between the seal member 38D and the frame section 14. The seal member 38 can be incorporated into the frame section 14 as an integral piece during a plastic molding process. Other mechanical engagement configurations which are well known in the art may be used for the attachment of the seal member 38 to the frame section 14 and will not be further described.

Figure 2:
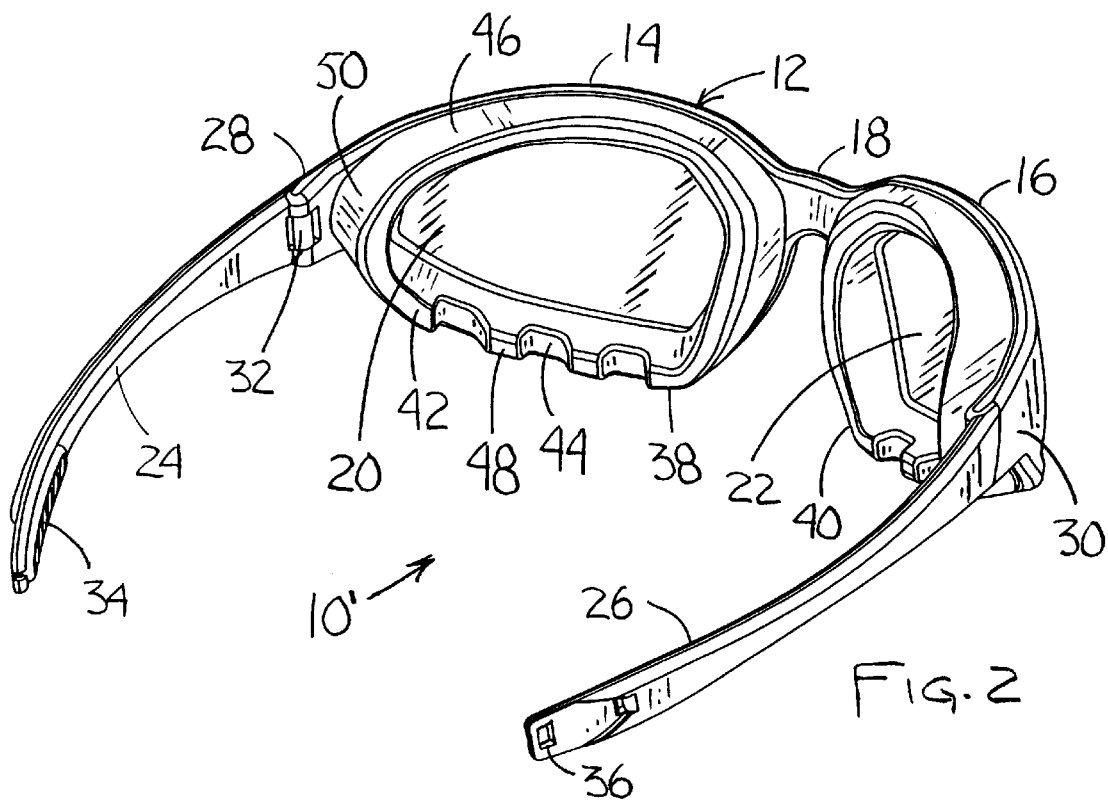
FIG. 2 is a perspective view of protective eyewear according to a second embodiment of the present invention, showing the ventilation channels formed on the contacting surface of the seal member, and positioned only in the bottom section thereof.

FIG. 2 illustrates a second embodiment of the present invention in which a eyewear structure indicated by numeral reference 10' has a configuration similar to that of the eyewear structure 10 in FIG. 1. The components and features of the eyewear structure 10' similar to those of the eyewear structure 10 are indicated by similar numeral references and will not be redundantly described. The difference between the eyewear structures 10 and 10' lies in that the seal member 38 of the eyewear structure 10' has the ventilation channels 44 positioned only in the lower section 48 of the seal member 38. This embodiment illustrates that the number and locations of the ventilation channels 44 formed on the contacting surface 42 of the seal member 38 can be arranged differently from the eyewear structure 10 in FIG. 1. However, in all configurations it is preferable to have at least one of the ventilation channels 44 located at a lowest position of the seal member 38 in order to facilitate the drainage of sweat and any other liquid which may otherwise remain within the enclosure defined by the seal member 38.

Figure 3:
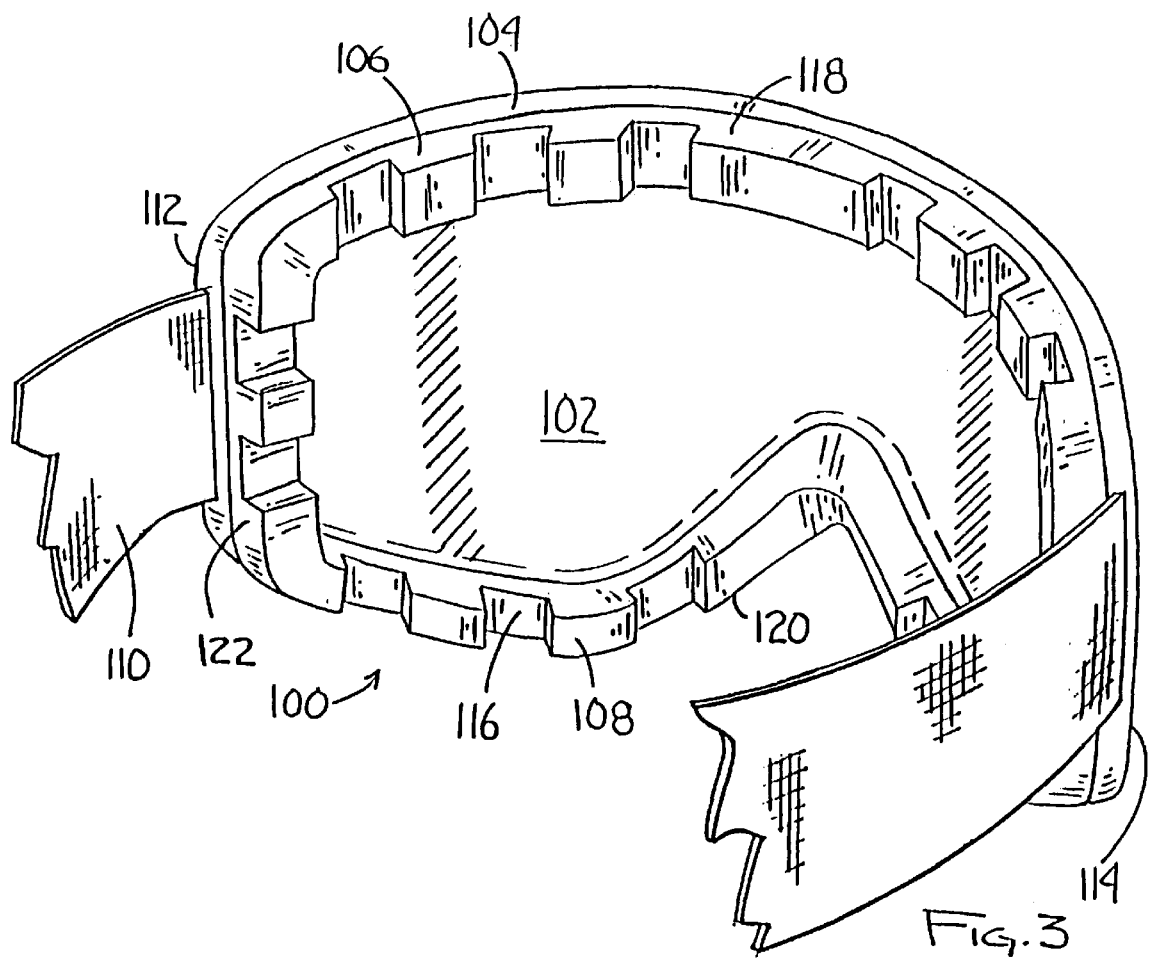
FIG. 3 is a partial perspective view of protective goggles according to a third embodiment of the present invention, showing the protective goggles having a one-piece lens and a seal member with ventilation.

FIG. 3 illustrates a third embodiment of the present invention in which a goggles structure, generally indicated by numeral reference 100, includes a single lens 102, a frame 104 securing the single lens 102 and a seal member 106. The frame 104 has an annular flange (not shown) which engages the periphery of the single lens 102 so that the single lens 102 is securely affixed in the frame 104 in a manner well known in the art, and will not be further described. The seal member 106 is attached to the inner side of the frame 104 and has a contacting surface 108 thereon. The combination of the single lens 102, the frame 104 and the seal member 106 is contoured such that the contacting surface 108 of the seal member 106 contacts the face of a user in a comfortable manner and the seal member thereby forms a substantial enclosure between the single lens 102 and the face of the user when the goggles structure 100 is worn.

An elastic strap 110 is attached to the opposite sides 112, 114 of the frame 106 for holding the goggles structure 100 on the head of the user.

A plurality of ventilation channels 116 are formed on the contacting surface 108 of the seal member 106 in the top section 118 and bottom section 120 as well as in side sections 122. The ventilation channels 116 extend into the seal member 106 towards the single lens 102 to a depth not reaching the frame 104 and ensure free passage of air from the enclosure to the atmosphere when the user wears the goggles structure 100 and the seal member 106 is elastically deformed against the face of the user, as discussed with reference to the goggles structure 10 of FIG. 1. The material properties and mounting features of the seal member 108 are similar to those of seal member 38 discussed with reference to FIGS. 1 and 4A–4D, and will not be redundantly described herein.

The seal member 106 and the frame 104 can be incorporated into a single piece which is securely attached to the inner side of the single lens 102, for example, by means of adhesives. The elastic strap 110 is attached to the opposite sides of the single lens 102 which extends beyond the opposite sides of the integrated frame 104 and seal member 106. The elastic strap 110 can also be made from two separate sections of non-elastic materials with adjustable fastening means attached thereto. Those features are well known in the prior art and will not be further described herein.

It should be noted that the ventilation channels 116 extend into the seal member 106 towards the single lens 102 to a maximum depth not reaching the single lens 102, when the frame 104 and the seal member 106 are incorporated into an integral piece and the integral piece is attached to the inner side of the single lens 102.

Modifications and improvements to the above-described embodiments of the present invention may become apparent to those skilled in the art. The foregoing description is intended to be exemplary rather than limiting. The scope of the invention is therefore intended to be limited solely by the scope of the appended claims.

We claim:

1. Eyewear comprising:
    at least one lens;
    a frame securing the at least one lens;
    means for attaching the eyewear to the head of a user;
    the frame including a hollow seal member having a surface for contacting the face of the user, the hollow seal member forming a substantial enclosure between the at least one lens and the face of the user when the surface of the hollow seal member contacts the face of the user; and
    at least one ventilation channel formed in the hollow seal member on the surface for contacting the face of the user, to ensure free passage of air from the enclosure to the atmosphere when the user wears the eyewear.

2. The eyewear as claimed in claim 1 wherein the ventilation channel is one of a plurality of ventilation channels in the hollow seal member.

3. The eyewear as claimed in claim 2 wherein at least one of the ventilation channels is located in a bottom section of the hollow seal member.

4. The eyewear as claimed in claim 3 wherein at least one of the ventilation channels is located in a top section of the hollow seal member.

5. The eyewear as claimed in claim 1 wherein the hollow seal member comprises a closed chamber containing air therein to increase the resiliency of the hollow seal member.

6. The eyewear comprising:
    a pair of lenses;
    a frame securing the respective lenses;
    means for attaching the eyewear to the head of a user;
    a pair of hollow seal members attached to the frame corresponding to the respective lenses, each hollow seal member having a surface for contacting the face of the user, thereby forming a substantial enclosure between a corresponding one of the lenses and the face of the user when the surface of the hollow seal member contacts the face of the user; and
    at least one ventilation channel formed in each of the hollow seal members on its surface for contacting the face of the users to ensure free passage of air from the enclosure to the atmosphere when the user wears the eyewear.

7. The eyewear as claimed in claim 6 wherein the at least one ventilation channel is one of a plurality of ventilation channels of each hollow seal member.

8. The eyewear as claimed in claim 7 wherein each hollow seal member is attached to the frame around a corresponding lens in a sealing manner.

9. The eyewear as claimed in claim 7 wherein a number of the ventilation channels are located in a bottom section of each hollow seal member.

10. The eyewear as claimed in claim 7 wherein a number of the ventilation channels are located in both a bottom section and a top section of each hollow seal member.

11. The eyewear as claimed in claim 6 wherein the hollow seal members are made of an elastomeric material.

12. The eyewear as claimed in claim 6 wherein the hollow seal members are made of semi-solid plastic material in a molding process.

13. The eyewear as claimed in claim 6 wherein the means for attaching the eyewear to the head of the user comprise a pair of temples pivotally attached to opposite sides of the frame.

14. The eyewear as claimed in claim 13 wherein each of the temples comprises an aperture at a free end thereof for attaching a retention strap.

15. The eyewear as claimed in claim 6 wherein the means for attaching the eyewear to the head of the user comprise a retention strap attached to opposite sides of the frame.

16. The eyewear as claimed in claim 6 wherein the hollow seal member comprises a closed chamber containing air therein to increase the resiliency of the hollow seal member.

17. The eyewear as claimed in claim 6 wherein the ventilation channel extends into the hollow seal member towards the corresponding lens and terminates before reaching the frame.

* * * * *